United States Patent
Biedermann et al.

(10) Patent No.: US 6,679,920 B2
(45) Date of Patent: Jan. 20, 2004

(54) DEVICE AND METHOD FOR REMOTE MAINTENANCE OF AN ELECTRONICALLY CONTROLLABLE PROSTHESIS

(75) Inventors: Lutz Biedermann, Villingen (DE); Wilfried Matthis, Weisweil (DE); Christian Schulz, Mittweida (DE)

(73) Assignee: Biedermann Motech GmbH (DE)

( * ) Notice: Subject to any disclaimer, the term of this patent is extended or adjusted under 35 U.S.C. 154(b) by 13 days.

(21) Appl. No.: 09/936,619

(22) PCT Filed: Jan. 5, 2001

(86) PCT No.: PCT/EP01/00078
§ 371 (c)(1),
(2), (4) Date: Sep. 11, 2001

(87) PCT Pub. No.: WO01/50986
PCT Pub. Date: Jul. 19, 2001

(65) Prior Publication Data
US 2002/0161451 A1 Oct. 31, 2002

(30) Foreign Application Priority Data
Jan. 11, 2000 (DE) .......................... 100 00 781

(51) Int. Cl.[7] .............................. A61F 2/64; A61F 2/68
(52) U.S. Cl. .............................................. 623/24; 623/44
(58) Field of Search ............................... 623/24, 44

(56) References Cited

U.S. PATENT DOCUMENTS

| | | | |
|---|---|---|---|
| 4,209,860 A | 7/1980 | Graupe | 3/1.1 |
| 5,383,939 A | 1/1995 | James | 623/24 |
| 5,413,611 A | 5/1995 | Haslam, II et al. | 623/25 |
| 5,443,524 A | 8/1995 | Sawamura et al. | 623/24 |
| 5,704,945 A | 1/1998 | Wagner et al. | 623/44 |
| 5,888,212 A | 3/1999 | Petrofsky et al. | 623/24 |
| 5,893,891 A | * 4/1999 | Zahedi | 623/24 |
| 6,423,098 B1 | 7/2002 | Biedermann | 623/24 |
| 6,436,058 B1 | * 8/2002 | Krahner et al. | 600/587 |
| 2002/0029784 A1 | * 3/2002 | Stark et al. | 128/898 |
| 2002/0143405 A1 | * 10/2002 | Davalli et al. | 623/24 |

FOREIGN PATENT DOCUMENTS

| | | |
|---|---|---|
| DE | 43 18 901 | 1/1994 |
| DE | 694 15 397 T2 | 12/1994 |
| DE | 195 06 426 C1 | 11/1996 |
| DE | 195 21 464 A1 | 3/1997 |
| DE | 197 54 690 A1 | 7/1999 |
| EP | 0 628 296 B1 | 12/1998 |
| GB | 2 334 891 A | 9/1999 |
| WO | WO 96/41599 | 12/1996 |

OTHER PUBLICATIONS

Med. Orth. Tech. 117 (1997) 31–35 (no translation).

* cited by examiner

Primary Examiner—David H. Willse
Assistant Examiner—Javier S Blanco
(74) Attorney, Agent, or Firm—George W. Neuner; Edwards & Angell, LLP

(57) ABSTRACT

A device and a method for remote maintenance of an electronically controllable prosthesis (1) are provided. The prosthesis comprises a controller in which operating and/or movement data characterizing the prosthesis are detected and are then transmitted to a remote maintenance device (20) with a storage and evaluation unit (20). Remote maintenance of the prosthesis using the detected data is possible via a remotely located remote control unit (23) that can access the storage and evaluation unit via the telephone network. Corrected operational data are transmitted from the storage and evaluation unit (20) back to the controller of the prosthesis.

19 Claims, 2 Drawing Sheets

DEVICE AND METHOD FOR REMOTE MAINTENANCE OF AN ELECTRONICALLY CONTROLLABLE PROSTHESIS

CROSS-REFERENCE TO RELATED APPLICATIONS

This is a 371 of PCT/P01/00078.

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not Applicable.

BACKGROUND OF THE INVENTION (1) Field of the Invention

The present invention concerns a device and a method for remote maintenance of an electronically controllable prosthesis.

(2) Description of Related Art

Electronically controllable prostheses are known, for example in the form of leg prostheses with an artificial knee joint as shown in Med. Orth. Tech. 117 (1997), pages 31 to 35. In these prostheses, the control parameters are determined and programmed in dependency of movement data that characterize a movement of the wearer of the prosthesis. However, to set the control data for an optimum gait pattern it is necessary for an orthopedics technician to observe the patient wearing the prosthesis while he or she is walking and to set the control parameters in dependency of these observations. The prosthesis is then controlled with the optimum control data determined during the observations.

There is a problem in that changes can occur to the walking behaviour of the prosthesis wearer during daily use of the prosthesis, for example the gait pattern changes as a result of changes to the weight of the prosthesis wearer or when other shoes are worn. The prosthesis is then no longer set optimally and the prosthesis wearer must have the orthopedic technician carry out a new setting in order to be able to walk comfortably. This takes time and is a problem for the prosthesis wearer.

SUMMARY OF THE INVENTION

The task of the invention is to provide a device and a process which simplifies maintaining and resetting an electronically controllable prosthesis.

The task is solved by means of a device for remote maintenance of an electronically controllable prosthesis whereby the prosthesis has a controller 11 for detecting movement data characterizing a movement of the prosthesis wearer and for outputting of control data to the prosthesis, wherein the remote maintenance device 20 comprises a first data transmission device 21, which can be linked to the controller 11 of the prosthesis 1, through which movement and/or control data can be transmitted bidirectionally between the controller 11 of the prosthesis and the first data transmission device 21, a second data transmission device 22 for transmitting movement and/or control data to a remotely located remote control unit 23 and for receiving data from the remote control unit 23 and a storage device 24 for storing movement and/or control data and wherein the remote control unit 23 is linked to the second data transmission device 22 via a data transmission network.

The invention also provides a method for remote maintenance of an electronically controllable prosthesis with the steps:

a) detecting data characterizing the operation of the prosthesis while the prosthesis is being worn;

b) transmitting the detected data to a remote maintenance device 20 comprising a storage and evaluation device;

c) accessing the data stored in the storage and evaluation device through a remote control unit 23 via a data transmission network;

d) assessing and, where necessary, updating the detected data;

e) transmitting the updated data to the storage and evaluation device via the data network; and f) transmitting the updated data from the storage and evaluation device 20 to the prosthesis.

Preferred embodiments of the invention provide a device comprising one or more of the following: a controller that controls an evaluation and/or transmission of the movement and/or control data in dependence on a preset program; one or more rechargeable batteries and the remote maintenance 20 comprising a device for charging the batteries when the prosthesis is connected to the device 20; an externally controllable clock 25 to enable synchronization with a a clock provided in the prosthesis; a display/input unit 26 for displaying the data concerning the prosthesis and for entering commands; and a controller designed so that it initiates communication via the second data transmission device 22 with the remote control unit 23 if the movement and/or control data deviate from default data. In other preferred embodiments, the remote maintenance takes place via the telephone network, and/or the prosthesis detects movement data over a preset period of time and these movement data are evaluated in the storage and evaluation device 20 and the data characterizing the operation of the prosthesis is corrected using the movement data; and/or the remote maintenance is carried out when the prosthesis has been removed.

Further characteristics and expediencies of the invention result from the description of an embodiment by means of the figures.

DETAILED DESCRIPTION OF THE INVENTION INCLUDING PREFERRED EMBODIMENTS

Figure 1:
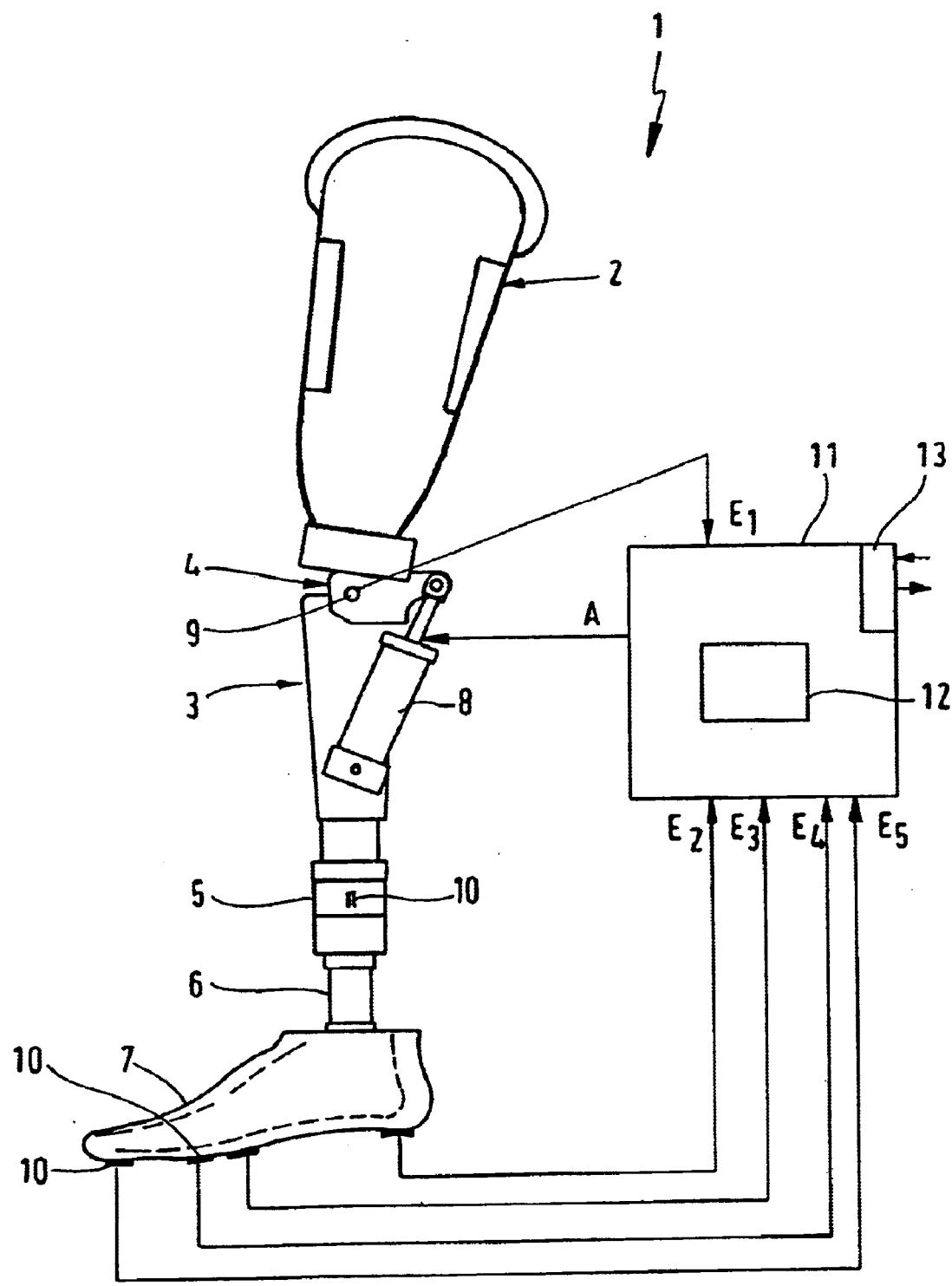
FIG. 1 a schematic representation of a leg prosthesis with an artificial knee joint and the appropriate controller.

As can be seen in FIG. 1, the prosthesis 1 comprises the familiar thigh part 2 and lower leg part 3 and a knee joint 4 that links the two. The lower leg part 3 has a shin part 5 with an lower leg tube 6 and a foot part 7 linked thereto.

The foot part 7 contains a leaf spring that is not shown in the illustration to enable a springy walk. The knee joint 4 comprises a damping element in the form of a hydraulic piston cylinder device 8. The leg prosthesis also has a number of sensors for measuring movement and force. Knee joint 4 has a knee angle sensor to record the knee angle during movements of the prosthesis wearer. In the area of the sole or alternatively at shin part 5 or the lower leg tube 6 there are force sensors for recording the forces that take effect when walking with the prosthesis. Depending on the functionality, there are 5 acceleration sensors installed in the shin part 5.

To control the flexion response of the knee joint 4 a control device 11 is provided that has a number of inputs $E_1$, $E_2$, $E_3$, $E_4$ to receive signals from the sensors described above. In addition, the control device 11 contains a real-time clock (not shown) and a data memory and microprocessor unit 12 in which the measured sensor signals, referred to below as the movement data, are stored over a preset period of movement of the prosthesis wearer and in which in addition control data, for example in the form of control parameters for controlling the operations of the prosthesis, are stored. The control device is linked to the piston cylinder device 8 of the knee joint through an output A through which the control data are sent to the piston cylinder device. In addition, the control device is linked through an interface 13 to the device for remote maintenance described below. An exchange of movement data and control data with the device for remote maintenance takes place via interface 13.

The controller 11 is linked to the body of the prosthesis wearer, for example it is integrated into the prosthesis itself or is worn over a belt on the prosthesis wearer's body. The artificial leg also has rechargeable batteries that are not shown here.

The control data saved to the controller are fixed on the initial setting of the prosthesis by an orthopedic technician after observing the way the prosthesis wearer walks.

Figure 2:
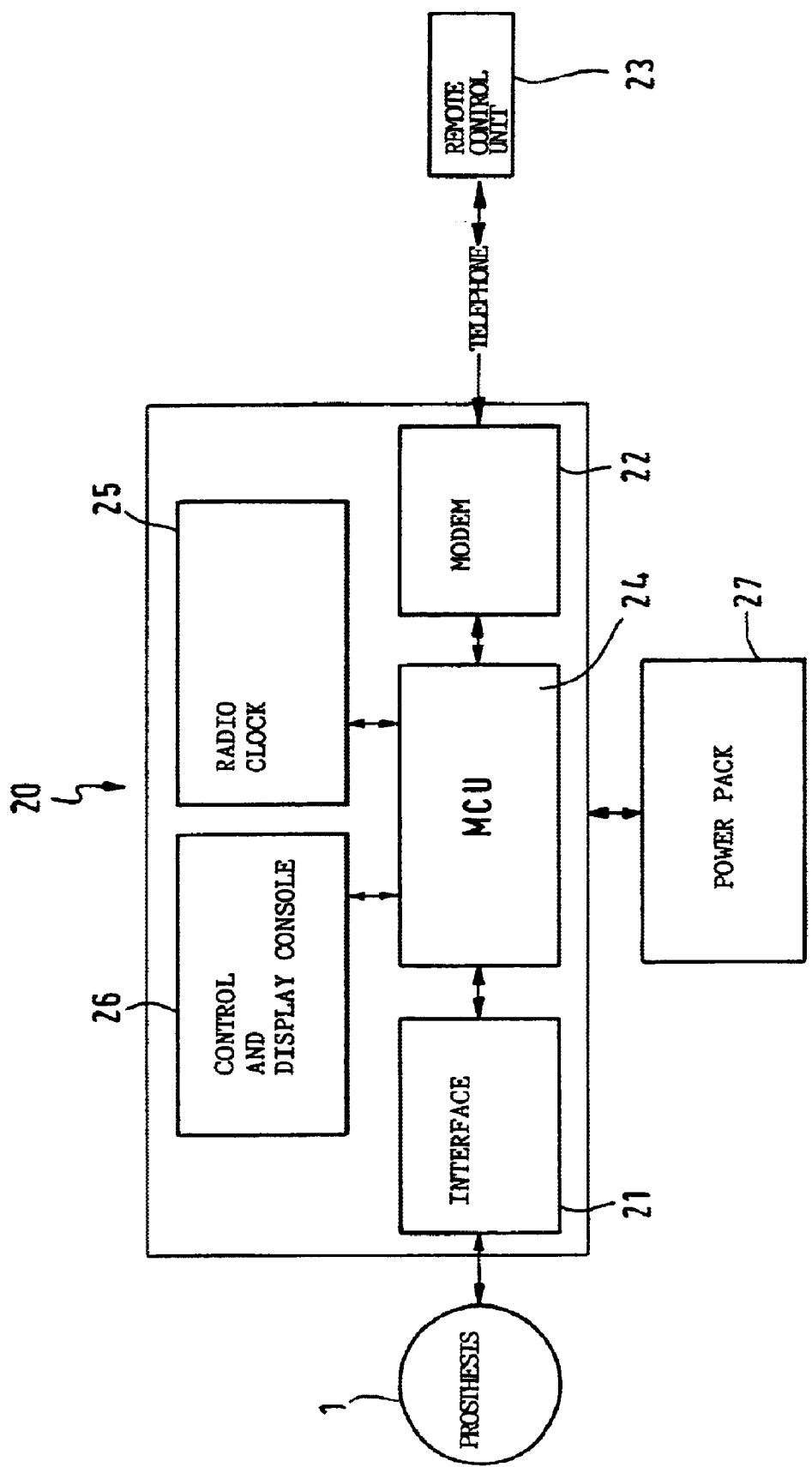
FIG. 2 a schematic representation of a device in accordance with the present invention for the remote maintenance of an electronically controllable prosthesis

FIG. 2 shows a remote maintenance device 20, or docking station, in accordance with the present invention, for the remote maintenance of the artificial leg described in FIG. 1. The remote maintenance device 20 permits the prosthesis controller 11 to be connected and control and movement data of the prosthesis to be collected, evaluating, processing and if necessary with an update of the data externally via a data network and feedback of the amended data to the controller 11 of the prosthesis. For this purpose the remote maintenance device 20 has an interface 21 through which the controller 11 can be linked to the remote maintenance device 20 and through which not only the movement data but also control data can be transmitted in both directions between the device 20 and the controller 11 in accordance with a defined transmission protocol. In addition, a remote data transmission device 22 is provided for transmitting movement and/or control data to an external, remotely located remote control unit 23 via a data network, e.g. the telephone network. The remote data transmission device 22 is designed, e.g., as a modem or an ISDN card. The remote control unit 23 is, for example, a PC that is linked to the data network.

The remote maintenance device 20 also contains a micro controller unit (MCU) 24 that functions as a central control and data storage device. The MCU 24 controls the interface 21 and the remote data transmission device 22 and stores the movement and control data. In addition, the MCU 24 has one or more preselectable programs for processing the data. The MCU 24 is also linked to an externally controlled clock 25, e.g. a radio clock, for synchronizing the time with the real-time clock in the controller 11 of the prosthesis. There is also a control and display panel 26 to enable the movement and/or control data to be displayed or evaluated and to enable commands and/or data to be entered. The remote maintenance device is also linked to a current or voltage supply in the form of a power pack 27 which permits a standby power supply for the prosthesis 1 when this is connected via interface 21 to the remote maintenance device 20 and/or allows the rechargeable batteries for the prosthesis to be charged.

A PC, which can be set up in the prosthesis wearer's own home, or a portable computer in the form of a laptop that has the appropriate elements as described, can be used as the remote maintenance device 20. The remote control unit 23 is expediently located on the premises used by the orthopedic technician and operated by him or her.

A program stored in the MCU 24 allows remote service of the prosthesis via the remote control unit 23 and the data network. The functions modules of this program will be described below by means of the operations.

The operation of the remote maintenance device 20 and the procedure in accordance with the present invention are as follows: after removing the prosthesis at home the prosthesis wearer connects the controller 11 of the prosthesis to the remote maintenance device 20. While the prosthesis is connected to the remote maintenance device 20, it is powered by the power pack 27 and/or the batteries are recharged. The controller 11 of the prosthesis then transmits the current control parameters and the movement data that were recorded over a predefined period of time to remote maintenance device 20. Communication between the remote control unit 23 and the remote maintenance device 20 via a data network is initiated either by the prosthesis wearer himself/herself by entering an appropriate command via the control and display panel 26, or the remote maintenance device 20 starts communicating with the remote control unit 23 through the MCU 24 at preset times. Alternatively, the remote control unit 23 can start to communicate with the remote maintenance device 20 at preset times.

After the connection with the remote control unit 23 is set up, the prosthesis is detected and specified by means of preset identification data. The movement and control data transmitted by means of the controller of the prosthesis are stored in the remote maintenance device 20 and subjected to a preliminary evaluation. The orthopedic technician can access the movement and control data stored in the remote maintenance device 20 via the remote control unit 23 and thus through the remote data transmission device 22, evaluate the data and carry out predefined operations with the data and in particular update and therefore correct the control data, i.e. the control parameters for the prosthesis. These updated or new control data are transmitted via interface 21 to the controller 11 of the prosthesis.

The remote maintenance program stored in the MCU 24 as the following modules and/or functions that are carried out in addition to the basic principle described above of data transmission from the prosthesis to the device and from there to a external receiver and vice versa. For example, the prosthesis can be supplied optionally with power in the device 20 through the power pack 27 and at the same time the batteries can be charged for subsequent use. The movement data can be evaluated in advance, whereby time differences of the prosthesis clock and the radio clock are taken into account as well. In the event of power failure the prosthesis clock can be corrected. At preset intervals the program carries out a complete storage of all prosthesis data that then serve as backup. The orthopedics technician can ask for information on the operational status of the prosthesis and on its utilization by accessing via the data network after entering a code number. There is also the facility that the data transmission device only reports to the remote control unit 23 if the remote maintenance program itself detects faults in the prosthesis.

Through storing the movement and control data in the remote maintenance device 20, i.e. outside the prosthesis, it is possible to carry out an analysis of gait and activities offline, that is, when the prosthesis is not connected to the remote maintenance device 20. By storing the movement and/or control data in the remote maintenance device 20 it is also possible to exchange data with the remote control unit 23, when the prosthesis is removed after transmission of the current movement and control data from the remote maintenance device 20. Online remote maintenance is also possible in which the prosthesis wearer does not remove the prosthesis but the control data and/or movement data are sent only to the remote control unit 23 while the prosthesis is being worn and an assessment and where necessary correction than takes place. Using the control and display panel it is possible to inform the prosthesis wearer of any faults after the prosthesis is attached so that he or she can then make adjustments themselves.

This means that with the device and procedure for remote maintenance as described above it is possible to subject an artificial leg to remote maintenance without the prosthesis wearer having to go in person to an orthopedics technician to have his/her prosthesis adjusted while walking.

In a further embodiment the remote control unit 23 is designed so that it can be used for remote maintenance of more than one prosthesis.

What is claimed is:

1. A device for remote maintenance of an electronically controllable prosthesis, the prosthesis comprising a controller for detecting movement data characterizing a movement of the prosthesis wearer and for outputting of control data to the prosthesis, the remote maintenance device comprising:
    a first data transmission device, which can be linked to the controller of the prosthesis, through which movement and/or control data can be transmitted bidirectionally between the controller of the prosthesis and the first data transmission device;
    a second data transmission device for transmitting movement and/or control data to a remotely located control unit and for receiving data from the remote control unit; and
    a storage device for storing movement and/or control data;
    wherein the remote control unit is linked to the second data transmission device via a data transmission network.

2. A device in accordance with claim 1, wherein the prosthesis further comprises one or more rechargeable batteries and wherein the device further comprises a charging component for charging the rechargeable batteries when the prosthesis is connected to the device.

3. A device in accordance with claim 2, wherein the controller of the prothesis further comprises a clock and the device further comprises an externally controllable clock to enable synchronization with said clock provided in the prosthesis.

4. A device in accordance with claim 2, further comprising a display/input unit for displaying the data concerning the prosthesis and for entering commands.

5. A device in accordance with claim 2, wherein the device is structured and arranged so that the controller initiates communication via the second data transmission device with the remote control unit when the movement and/or control data deviate from a default data.

6. A device in accordance with claim 1, further comprising a controller that controls an evaluation and/or transmission of the movement and/or control data in accord with a preset program.

7. A device in accordance with claim 6, wherein the controller of the prothesis further comprises a clock and the device further comprises an externally controllable clock to enable synchronization with said clock provided in the prosthesis.

8. A device in accordance with claim 6, further comprising a display/input unit for displaying the data concerning the prosthesis and for entering commands.

9. A device in accordance with claim 6, wherein the device is structured and arranged so that the controller initiates communication via the second data transmission device with the remote control unit when the movement and/or control data deviate from a default data.

10. A device in accordance with claim 1, wherein the controller of the prothesis further comprises a clock and the device further comprises an externally controllable clock to enable synchronization with said clock provided in the prosthesis.

11. A device in accordance with claim 10, further comprising a display/input unit for displaying the data concerning the prosthesis and for entering commands.

12. A device in accordance with claim 10, wherein the device is structured and arranged so that the controller initiates communication via the second data transmission device with the remote control unit when the movement and/or control data deviate from a default data.

13. A device in accordance with claim 1, further comprising a display/input unit for displaying the data concerning the prosthesis and for entering commands.

14. A device in accordance with claim 13, wherein the device is structured and arranged so that the controller initiates communication via the second data transmission device with the remote control unit when the movement and/or control data deviate from a default data.

15. A device in accordance with claim 1, wherein the device is structured and arranged so that the controller initiates communication via the second data transmission device with the remote control unit when the movement and/or control data deviate from a default data.

16. A method for remote maintenance of an electronically controllable prosthesis, the method comprising the steps of:
    a) detecting data characterizing the operation of the prosthesis while the prosthesis is being worn;
    b) transmitting the detected data to a remote maintenance device comprising a data storage and evaluation device;
    c) accessing the data stored in the data storage and evaluation device through remote control unit via a data transmission network;
    d) assessing and, when necessary, updating the stored data;
    e) transmitting, when necessary, updated data to the data storage and evaluation device via the data transmission network; and
    f) transmitting the updated data from the storage and evaluation device to the prosthesis.

17. A method in accordance with claim 16, wherein the data transmission network is a telephone network.

18. A method in accordance with claim 16, wherein the detecting step comprises detecting movement data over a preset period of time and, the method further comprises evaluating the movement data in the data storage and evaluation device and correcting the data characterizing the operation of the prosthesis using the movement data.

19. A method in accordance with claim 16, further comprising removing the prosthesis to carry out the remote maintenance.

* * * * *